(12) United States Patent
Youn et al.

(10) Patent No.: US 8,676,334 B2
(45) Date of Patent: Mar. 18, 2014

(54) PERIPHERAL NERVE INTERFACE SYSTEM AND METHOD FOR PROSTHETIC HAND CONTROL

(71) Applicants: In Chan Youn, Seoul (KR); Kui Won Choi, Seoul (KR); Jun-Kyo Francis Suh, Seoul (KR); Kwang Meyung Kim, Seoul (KR); Jun Uk Chu, Cheongwon-gun (KR); Sung Min Han, Uijeongbu-si (KR); Kang Il Song, Seoul (KR); Heui Chang Lee, Gwacheon-si (KR); Jong Woong Park, Seoul (KR)

(72) Inventors: In Chan Youn, Seoul (KR); Kui Won Choi, Seoul (KR); Jun-Kyo Francis Suh, Seoul (KR); Kwang Meyung Kim, Seoul (KR); Jun Uk Chu, Cheongwon-gun (KR); Sung Min Han, Uijeongbu-si (KR); Kang Il Song, Seoul (KR); Heui Chang Lee, Gwacheon-si (KR); Jong Woong Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/676,598

(22) Filed: Nov. 14, 2012

(65) Prior Publication Data
US 2013/0253606 A1 Sep. 26, 2013

(30) Foreign Application Priority Data

Mar. 20, 2012 (KR) .......................... 10-2012-0028346

(51) Int. Cl.
*A61N 1/00* (2006.01)

(52) U.S. Cl.
USPC ........................................... 607/48

(58) Field of Classification Search
USPC .................................................. 607/48, 118
See application file for complete search history.

(56) References Cited

U.S. PATENT DOCUMENTS

| 6,908,470 B2 | 6/2005 | Stieglitz et al. | |
|---|---|---|---|
| 2008/0228240 A1* | 9/2008 | Edell et al. | ...................... 607/48 |
| 2011/0137375 A1 | 6/2011 | McBride | |

FOREIGN PATENT DOCUMENTS

| JP | 2006-239447 | 9/2006 |
|---|---|---|
| JP | 2007-125104 | 5/2007 |
| JP | 2008-212652 | 9/2008 |
| KR | 10-0694282 B1 | 3/2007 |
| KR | 10-0765960 B1 | 10/2007 |
| KR | 10-1128341 B1 | 3/2012 |

* cited by examiner

*Primary Examiner* — Robert N Wieland
(74) *Attorney, Agent, or Firm* — NSIP Law (57) ABSTRACT

The present disclosure relates to peripheral nerve interface system and method for prosthetic hand control, which may measure, analyze and control efferent motor nerve signals and afferent sensory nerve signals by regenerating a peripheral nerve and control an artificial prosthetic hand by means of the measurement, analysis and control of the signals. For this, the peripheral nerve interface system according to an embodiment of the present disclosure includes: a nerve conduit connected to a terminal of a damaged peripheral nerve at a cut body portion; a prosthesis for substituting for the cut body portion; and a peripheral nerve interface unit electrically connected to the nerve conduit and the prosthesis to restore a function of the damaged peripheral nerve and control operations of the prosthesis by transmitting and receiving signals of the damaged peripheral nerve.

10 Claims, 7 Drawing Sheets

PERIPHERAL NERVE INTERFACE SYSTEM AND METHOD FOR PROSTHETIC HAND CONTROL

CROSS-REFERENCE TO RELATED APPLICATION

This application claims priority to Korean Patent Application No. 10-2012-0028346, filed on Mar. 20, 2012, and all the benefits accruing therefrom under 35 U.S.C. §119, the contents of which in its entirety are herein incorporated by reference.

BACKGROUND

1. Field

The present disclosure relates to peripheral nerve interface system and method for prosthetic hand control, which may measure, analyze and control efferent motor nerve signals and afferent sensory nerve signals by regenerating a peripheral nerve and control an artificial prosthetic hand by means of the measurement, analysis and control of the signals.

2. Description of the Related Art

If a nerve is damaged, for example if a nerve is cut, stimuli generated in or out of a living body are not normally transferred, and so a seriously bad influence is exerted to an organism. The cutting may occur due to diseases such as arteriosclerosis, diabetes and Buerger disease, injuries caused by car accidents or industrial accidents, infections, tumors, congenital deformities or the like. The number of disabled persons suffering from congenital or acquired deformities is increasing every year, and the rehabilitation and return to the normal social life for disabled persons suffering from cutting become a great issue.

Most of disabled persons suffering from cutting rehabilitate by wearing a prosthetic hand, a prosthetic leg or an assist device and training. If such rehabilitating tools are used, a user may not easily feel a touching sense or conduct a complicated work such as writing. In addition, if a patient suffers from serious cutting, wearing and controlling such an assist device is substantially impossible.

Existing artificial prosthetic hand or prosthetic foot determines the intent of a behavior by means of body power or surface electromyogram but is disregarded by patients due to low recognition rate and malfunctions. In order to solve such problems, a technique for moving artificial prosthetic hand and foot according to the intention of a user is demanded. In other words, as one of methods using nerves remaining in a cut portion, a nerve control technique and a nerve feedback technique where a sensor is attached to artificial prosthetic hand and foot to feed sense information to the nerves are demanded.

In relation to existing nerve signal detection and stimulation, techniques such as a depth type, a planar type, a sieve type and a cuff type are being studied, but these techniques have limits as follows.

The planar type (which is also called Microelectrode Array (MEA)) is directed to measuring a nerve signal by means of nerve cell cultivation. However, since the planar type is generally utilized for studying a method for analyzing signals of a nerve system or a method for inputting information to a nerve system, it is not suitable to apply the planar type to a technique of connecting a nerve system and an artificial device.

The depth type represents a method of directly inserting an electrode into a nerve tissue and using the electrode. The electrode collects electric signals from surrounding nerves. However, an insertion-type electrode may cause necrosis or accumulations of surrounding cells due to a long time use, which may prevent active signals of nerves from being stably measured. In other words, due to the feature of nerves which are composed of several bundle-type efferent axons, there is a limit in distinguishing signals accurately.

The sieve type disclosed in U.S. Pat. No. 6,908,470 is called a nerve-regenerating electrode. The sieve type uses regenerating ability of nerves, where a sieve-shaped electrode is placed between cut nerves so that the efferent axons of the nerve cells are regenerated while passing between the sieve-shaped electrodes. By doing so, a nerve signal may be measured. However, the sieve electrode may be used only when being located between cut nerves, namely only when nerves are alive at both terminals, and so its application scope is limited.

The cuff type is directed to measuring a nerve signal by surrounding nerves directly. Since the cuff type measures a nerve signal from an outside of nerves surrounded by an insulator, it is difficult to measure an accurate signal and separate afferent and efferent signals.

Therefore, the existing methods described above have limits in detecting nerve signals of cut peripheral nerves composed of bundle-type efferent axons and freely controlling a prosthetic hand through stimulation.

RELATED LITERATURES

Patent Literature

U.S. Pat. No. 6,908,470

SUMMARY

The present disclosure is directed to making it possible to regenerate damaged peripheral nerves of a patient suffering from cutting and selectively detect, analyze, transfer and stimulate nerve signals. In addition, the present disclosure is directed to providing peripheral nerve interface system and method which controls a prosthetic hand accordingly so a disabled person suffering from cutting may undergo rehabilitation.

In one aspect, there is provided a peripheral nerve interface system, which includes: a nerve conduit connected to a terminal of a damaged peripheral nerve at a cut body portion; a prosthesis for substituting for the cut body portion; and a peripheral nerve interface unit electrically connected to the nerve conduit and the prosthesis to restore a function of the damaged peripheral nerve and control operations of the prosthesis by transmitting and receiving signals of the damaged peripheral nerve.

The nerve conduit may include: a support connected to the terminal of the damaged peripheral nerve; a channel formed in a body of the support and having a cavity shape; an electrode layer formed along an inner wall of the channel; and an external electrode electrically connected to the electrode layer, wherein a nerve cell may grow along the channel at the terminal of the damaged peripheral nerve, the nerve cell having grown along the channel may be electrically connected to the electrode layer, and a plurality of channels may be formed at the support.

The peripheral nerve interface unit may include: an internal module implanted into the damaged body portion and electrically connected to the nerve conduit; and an external module positioned out of the damaged body portion and electrically connected to the prosthesis, wherein the internal module and the external module may transmit and receive nerve signals to/from each other in a wireless communication manner.

The internal module may include: a first amplifying unit for amplifying the signal of the damaged peripheral nerve received through the nerve conduit; a first AD converter for converting the signal amplified by the first amplifying unit into a digital signal; a first digital signal processing unit for receiving and analyzing the digital signal converted by the first AD converter and transmitting the digital signal to the external module in a wireless communication manner, or receiving and analyzing the digital signal received from the external module and transmitting the digital signal to the grown nerve cell through the channel; a DA converter for converting the digital signal received by the first digital signal processing unit into an analog signal; a stimulating unit for transferring an electric stimulation signal to the grown nerve cell along the plurality of channels by using the analog signal converted by the DA converter; a multiplexer for electrically matching a plurality of nerve cells having grown along the plurality of channels according to an instruction of the first digital signal processing unit with the first amplifying unit and the stimulating unit; and a first communication unit for transmitting and receiving signals to/from the external module in a wireless communication manner.

The internal module may further include: a first battery unit for supplying power to the internal module; and a wireless power receiving unit for receiving power from the external module in a wireless manner and transferring the power to the first battery unit.

The peripheral nerve interface system may further include a nerve regenerating electrode connected to the damaged peripheral nerve, wherein the stimulating unit may transfer a nerve generating stimulation signal to the nerve regenerating electrode.

The first digital signal processing unit may adopt a multilayer perceptron algorithm The external module may include: a second communication unit for transmitting and receiving a signal to/from the internal module in a wireless communication manner; a second AD converter for converting an analog signal received by a sensor installed at the prosthesis into a digital signal; a second digital signal processing unit for analyzing and processing the signal of the peripheral nerve received by the second communication unit and transmitting the signal to the internal module through the second communication unit based on the signal received by the second AD converter; an embedded controller for controlling operations of the prosthesis based on the signal processed by the second digital signal processing unit; and a second amplifying unit for amplifying a control signal of the embedded controller and transferring the amplified control signal to the prosthesis.

The external module may include: a second battery unit for supplying power to the external module; and a wireless power transmitting unit for receiving power from the second battery unit and transmitting the power to the internal module in a wireless manner.

The prosthesis may include at least one sensor for detecting a sensory signal.

In another aspect, there is also provided a peripheral nerve interface method, which include: regenerating a nerve cell at a terminal of a damaged peripheral nerve of a cut body portion by using a nerve conduit; detecting an efferent motor nerve signal by using an internal module implanted in the cut body portion and electrically connected to the nerve conduit; transmitting the efferent motor nerve signal to an external module located out of the cut body portion; and controlling an operation of a prosthesis which substitutes for the cut body portion by using the external module.

The peripheral nerve interface method according to an embodiment of the present disclosure may further include: detecting, by a sensor installed at the prosthesis, an afferent sensory signal; analyzing, by the external module, the detected afferent sensory signal; receiving, by the internal module, the afferent sensory signal from the external module; and generating, by the internal module, an electric stimulation signal corresponding to the afferent sensory signal and transferring the electric stimulation signal through the nerve conduit to the nerve cell at the terminal of the peripheral nerve.

The peripheral nerve interface method according to an embodiment of the present disclosure may further include transferring, by the internal module, a nerve generating stimulation signal to a nerve regenerating electrode connected to the damaged peripheral nerve.

In the peripheral nerve interface method according to an embodiment of the present disclosure, the nerve conduit may include a porous polymer electrode, and the method may further: include selectively detecting the efferent motor nerve signal or the afferent sensory nerve signal by using the porous polymer electrode; and selectively transferring an electric stimulation signal to the nerve cell at the terminal of the damaged peripheral nerve, which may be performed by using a multilayer perceptron algorithm.

The peripheral nerve interface system and method according to the present disclosure may effectively regenerate peripheral nerves at a cutting portion by using a nerve conduit having a porous polymer electrode, a peripheral nerve interface unit and a prosthesis, and may effectively control a prosthesis such as a prosthetic hand by transmitting or receiving efferent motor nerve signals and afferent sensory nerve signals.

BRIEF DESCRIPTION OF THE DRAWINGS

The above and other aspects, features and advantages of the disclosed exemplary embodiments will be more apparent from the following detailed description taken in conjunction with the accompanying drawings in which.

| Detailed Description of Main Elements |  |
|---|---|
| 100: nerve conduit | 200: peripheral nerve interface unit |
| 220: internal module | 240: external module |
| 300: prosthesis | |

DETAILED DESCRIPTION

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art.

Figure 1:
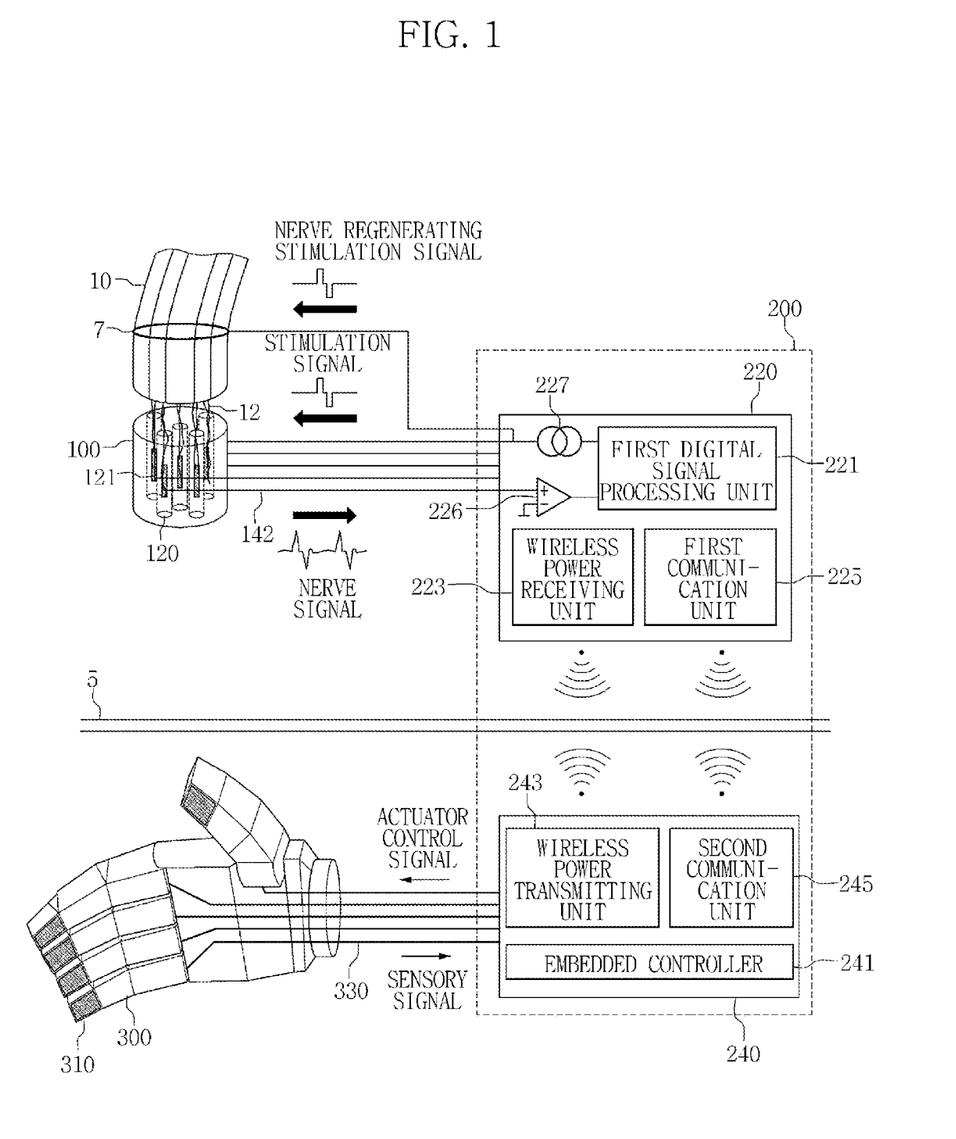
FIG. 1 is a schematic diagram showing a peripheral nerve interface system according to an embodiment of the present disclosure.

FIG. 1 is a schematic diagram showing a peripheral nerve interface system according to an embodiment of the present disclosure.

Referring to FIG. 1, the peripheral nerve interface system according to an embodiment of the present disclosure includes a nerve conduit 100, a peripheral nerve interface unit 200 and a prosthesis 300.

The nerve conduit 100 is electrically connected to a peripheral nerve 10 of a cut body portion to detect a nerve signal or transfer an electric stimulation signal. In detail, a plurality of channels 120 having a cavity shape are formed in the nerve conduit 100, and an electrode layer 121 is formed in the channel 120. The electrode layer 121 is electrically connected to an efferent axon 12 which is regenerated at a terminal of the peripheral nerve.

In particular, since the nerve conduit 100 has the plurality of channels 120, the nerve conduit 100 may connect a plurality of nerve cells of the regenerated efferent axon 12 to each electrode so that an efferent motor nerve signal is transferred to an internal module 220, described later, through a second connection unit 142 made of wire or the like. In addition, the nerve conduit 100 may receive a stimulation signal or a nerve generating stimulation signal from an internal module 220 of the peripheral nerve interface unit 200.

The nerve cell at the terminal of the peripheral nerve 10 may be regenerated and electrically connected to the nerve conduit 100, and a ring-shaped nerve regenerating electrode 7 is coupled to the peripheral nerve 10. The nerve regenerating electrode 7 plays a role of transferring a nerve-regenerating electric stimulation signal from the internal module 220 to the peripheral nerve 10.

Detailed configuration and operations of the nerve conduit 100 according to the present disclosure, which adopts a porous polymer electrode in order to selectively detect nerve signals of a plurality of nerve cells will be described later with reference to FIGS. 2 to 4.

The peripheral nerve interface unit 200 includes an internal module 220 and an external module 240 and the peripheral nerve interface unit 200 transmits or receives a nerve signal or an electric stimulation signal between the peripheral nerve 10 of the cut body portion and the prosthesis 300 connected to the cut body portion.

The internal module 220 is implanted in a body of a human or animal and electrically connected to the nerve conduit 100. Referring to FIG. 1, the internal module 220 is implanted in a skin 5 and includes a first digital signal processing unit 221, a wireless power receiving unit 223, a first communication unit 225, a first amplifying unit 226 and a stimulating unit 227.

The first amplifying unit 226 receives and amplifies an efferent motor nerve signal transferred from the nerve conduit 100. The first digital signal processing unit 221 analyzes the amplified efferent motor nerve signal and transmits the analyzed amplified efferent motor nerve signal through the first communication unit 225 to an external module 240, described later. In addition, the stimulating unit 227 plays a role of transferring the electric stimulation signal to the nerve conduit 100 according to an instruction of the first digital signal processing unit 221. The wireless power receiving unit 223 plays a role of receiving power from the external module 240 in a wireless manner and supplying the power to the internal module 220.

The external module 240 is located out of the body, namely the skin 5, and includes an embedded controller 241, a wireless power transmitting unit 243 and a second communication unit 245. Referring to FIG. 1, the external module 240 transmits or receives signals to/from the first communication unit 225 of the internal module 220 through the second communication unit 245. The wireless power transmitting unit 243 supplies power to the wireless power receiving unit 223 of the internal module 220 in a wireless manner. The embedded controller 241 generates an actuator control signal according to the efferent motor nerve signal received from the internal module 220 and controls a joint of the prosthesis 300.

The prosthesis 300 is an artificial assisting tool which assists the cut body portion of a patient and may be a robot module such as a prosthetic hand and a prosthetic foot. At least one sensor 310 for sensing sensory signals of a body may be installed at the prosthesis 300, and at least one sensor 310 is connected to the external module 240 through the third connection unit 330.

General operations of the peripheral nerve interface system according to the embodiment of the present disclosure will be described below.

First, the efferent axon 12 of the peripheral nerve 10 grows through the channel 120 and is connected to the electrode layer 121. The electrode layer 121 is connected to the internal module 220 through the second connection unit 142, and the efferent motor nerve signal is transferred to the first amplifying unit 226 and then amplified. The amplified signal is transferred to the external module 240 through the first digital signal processing unit 221 and the first communication unit 225.

The second communication unit 245 of the external module 240 receives the efferent motor nerve signal and transmits the efferent motor nerve signal to the embedded controller 241. The embedded controller 241 generates an actuator control signal corresponding to the efferent motor nerve signal to control a joint operation of the prosthesis 300.

In addition, at least one sensor 310 capable of sensing sensory signals such as a touch signal is installed at the prosthesis 300. The sensor 310 may be configured with various sensors such as a pressure sensor and a temperature sensor. If the sensor 310 senses a sensory signal, the sensory signal is transferred through the third connection unit 330 to the external module 240, and the external module 240 transfers the sensory signal through the second communication unit 245 to the internal module 220. The first digital signal processing unit 221 of the internal module 220 which has received the sensory signal transmits an electric stimulation signal corresponding to the sensory signal through the stimulating unit 227 and the second connection unit 142 to the nerve conduit 100.

Figure 2:
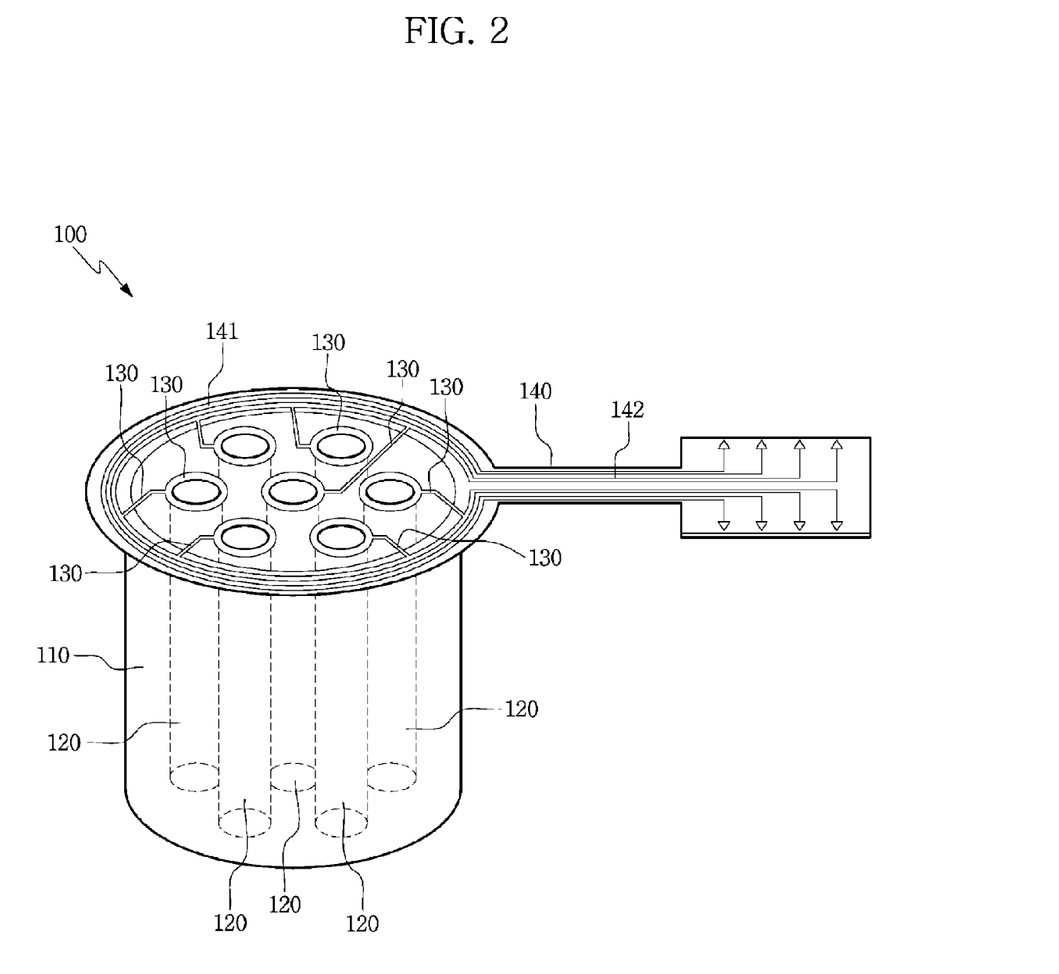
FIG. 2 is a perspective view showing a nerve conduit applied to the peripheral nerve interface system according to an embodiment of the present disclosure.

FIG. 2 is a perspective view showing a nerve conduit applied to the peripheral nerve interface system according to an embodiment of the present disclosure.

Referring to FIG. 2, the nerve conduit 100 includes a cylindrical support 110 and a plurality of channels 120 formed in a body of the support 110 and having a cavity shape. As described later, an electrode layer 121 (see FIGS. 3 and 4) is formed at each channel 120 along the inner wall thereof.

The support 110 has a cylindrical body and is connected to a terminal of a cut nerve. The support 110 is made of polyurethane and is formed with a plurality of fibers. The material of the support 110 is not limited to the above, and a biofriendly material capable of forming a certain shape with a predetermined strength may be adopted as the support 110 of this embodiment.

The plurality of channels 120 are formed in the body of the support 110 in the length direction of the support 110. For convenience, the channels 120 are depicted with dotted lines.

An external electrode 130 is formed at an entrance of each of the plurality of channels 120 (namely, at the upper surface of the support 110). The external electrode 130 is electrically connected to the electrode layer 121 as described later, and is also electrically connected to a connection electrode 140 formed at the upper surface of the support 110.

The connection electrode 140 includes a ring-shaped first connection unit 141 formed along the upper circumference of the support 110 and a second connection unit 142 electrically connected to the first connection unit 141.

As shown in FIG. 2, the first connection unit 141 is electrically connected to the external electrodes 130 connected to each channel 120, and the second connection unit 142 is electrically connected to the internal module 220.

Figure 3:
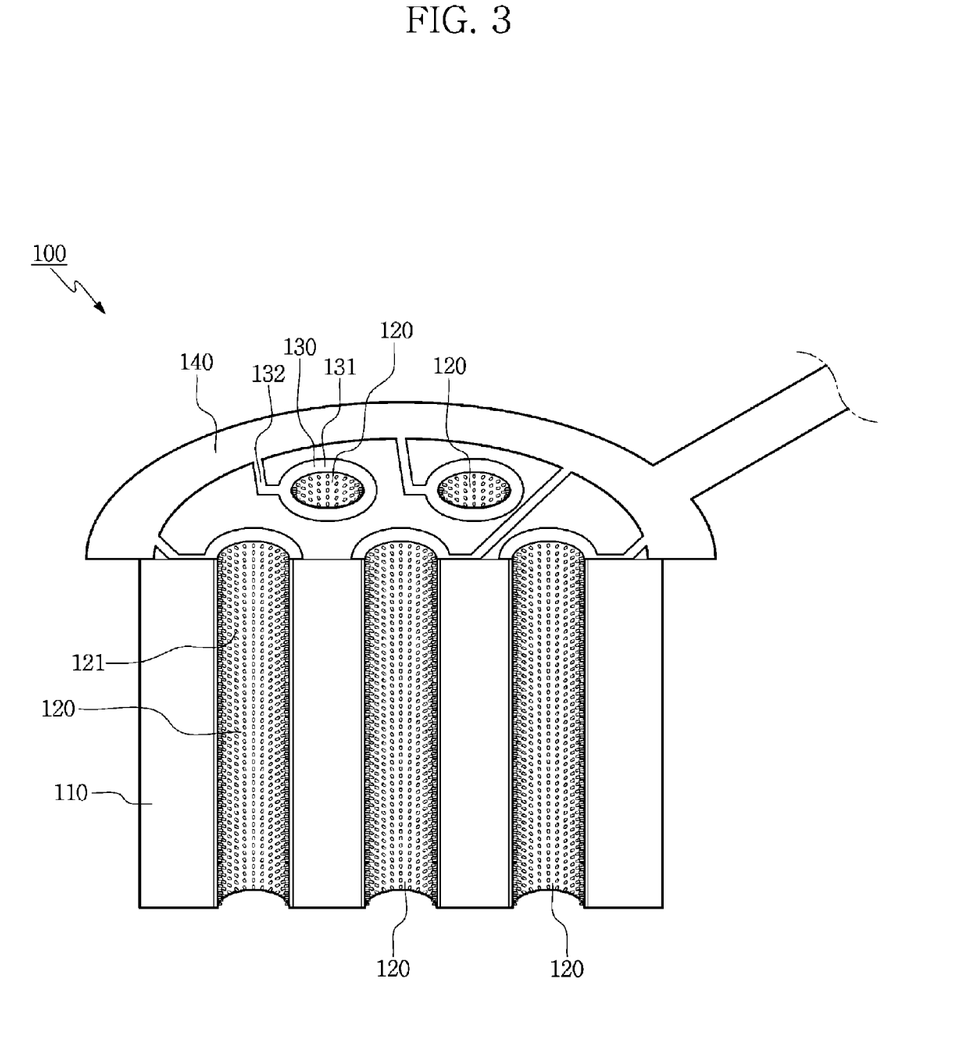
FIG. 3 is a sectioned perspective view showing the nerve conduit of FIG. 2.

FIG. 3 is a sectioned perspective view showing the nerve conduit of FIG. 2. In FIG. 3, the nerve conduit 100 is depicted as being cut by half in the length direction thereof.

As shown in FIG. 3, an electrode layer 121 is formed at the inner wall of the channel 120. According to this embodiment, the electrode layer 121 is formed with a plurality of nano fibers extending toward the center of the channel 120.

For convenience, it could be understood that the diameter of nano fibers and the distance between nano fibers are exaggerated in FIG. 3. The nano fibers may be formed more minutely and more densely depending on the manufacturing process condition.

In one embodiment, the nano fiber may be GaZnO obtained by doping zinc oxide (ZnO) with gallium (Ga), whose electric properties may be controlled. GaZnO is a ceramic material with excellent conductivity, and, when being used as an electrode, GaZnO has excellent biocompatibility due to low toxicity, different from general metals.

In order to distribute nano fibers in the channel 120 uniformly and use the distributed nano fiber layer as the electrode layer 121, this embodiment uses a so-called sol-gel process. The sol-gel process is used so that the nano fibers grow uniformly at the inner surface of the common channel 120, and an electric network is formed among the nano fibers so that the inside of the channel 120 has conductivity due to the nano fibers.

The sol-gel process is well known in the art and thus not described in detail here.

The external electrode 130 is formed at the entrance of each channel 120 and is electrically connected to the electrode layer 121. The external electrode 130 includes a first electrode unit 131 formed with a ring shape along the circumference of the entrance of the channel 120 and a second electrode unit 132 extending to be electrically connected to the first electrode unit 131.

The first electrode unit 131 is connected to a part of the electrode layer 121 exposed to the upper surface of the support 110 to make an electric connection to electrode layer 121, and the second electrode unit 132 is electrically connected to the first connection unit 141 of the connection electrode 140.

In this embodiment, the electrode layer 121 formed at the inner surface of each channel 120 and the external electrode 130 electrically connected thereto have the same configuration.

Hereinafter, the channel 120 and relevant configurations will be described in detail with reference to FIG. 4.

Figure 4:
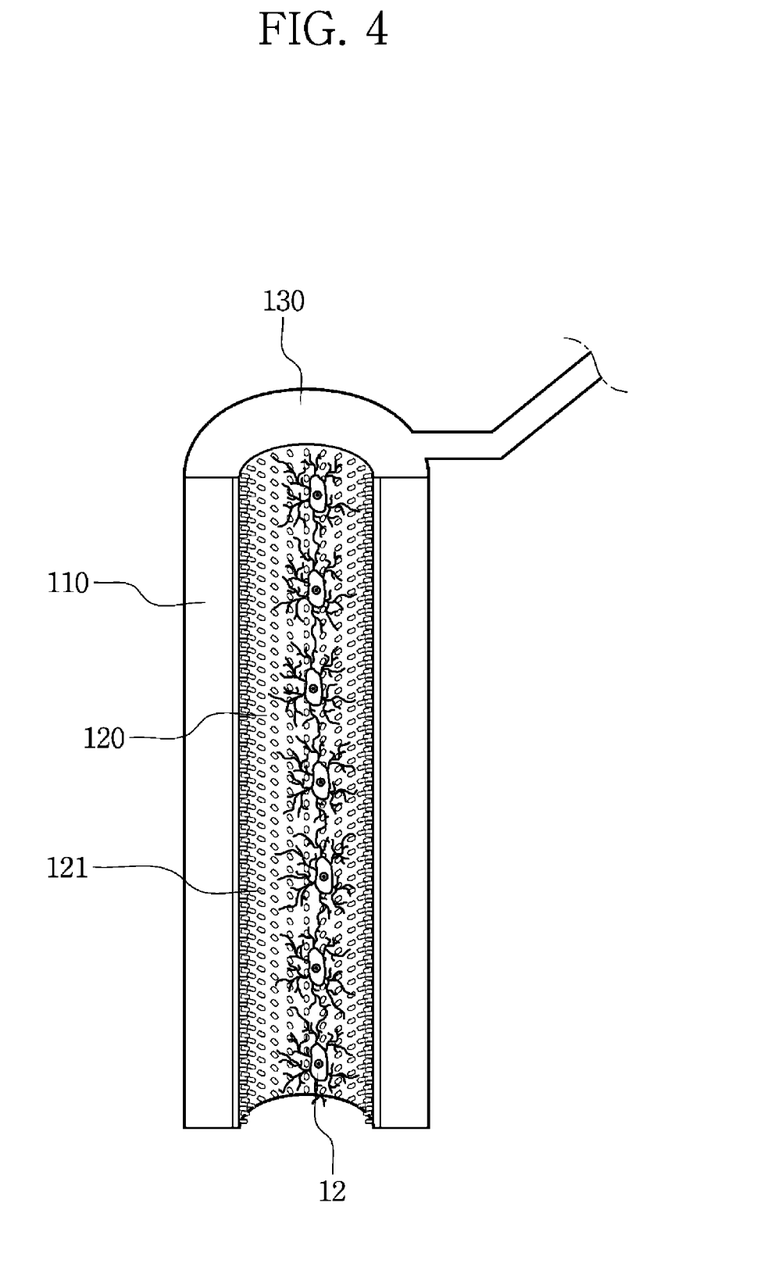
FIG. 4 is a cross-sectional view showing a part of the nerve conduit of FIG. 3.

FIG. 4 is a cross-sectional view showing a part of the nerve conduit of FIG. 3. FIG. 4 shows a single channel 120, and other channels have the same configuration.

As shown in FIG. 4, a nerve cell (namely, the efferent axon 12) grows into the channel 120 from the terminal of a cut nerve. Even though FIG. 4 shows only one strand of the efferent axon 12, multiple strands of the nerve cells may grow (be regenerated) in the channel 120. The method for regenerating nerve cells is already well know in the art and thus is not described in detail here since the method is not included in the scope of the present disclosure.

The efferent axon 12 grows into the channel 120 along the inner wall of the channel 120 by using nano fibers as a support material. Since nano fibers are used as the support material, the efferent axon 12 is firmly fixed in the channel 120.

As described above, since the nano fibers form the electrode layer 121 at the inner wall of the channel 120, the efferent axon 12 is naturally electrically connected to the electrode layer 121.

Therefore, the efferent nerve signal transferred from the efferent axon 12 to the electrode layer 121 may be detected by the external electrode 130 and transferred to the outside through the connection electrode 140. In addition, the external electric signal transferred through the connection electrode 140 may be transferred to the efferent axon 12 through the external electrode 130 and the electrode layer 121.

According to this embodiment, a plurality of channels 120 may be formed in the support 110 simultaneously. In particular, since the nerve is composed of a plurality of nerve cell bundles which are respectively connected to different organs in general cases, by forming a plurality of channels 120 in the support 110 and allowing nerve cell bundles to selectively grow in each channel 120, the process of classifying and transferring nerve signals may be more easily performed.

The support 110 with the plurality of channels 120 are prepared by forming a plurality of channels 120 through a single cylindrical support 110 by means of an etching process or by binding several conduits formed in a single channel 120.

In order to selectively detect, analyze and transfer a plurality of nerve signals by using the nerve conduit 100 configured as above, the present disclosure uses a wireless communication manner and an artificial nerve network.

Hereinafter, the configuration and operations of the peripheral nerve interface unit 200 according to the present disclosure will be described in detail with reference to FIGS. 5 and 6.

Figure 5:
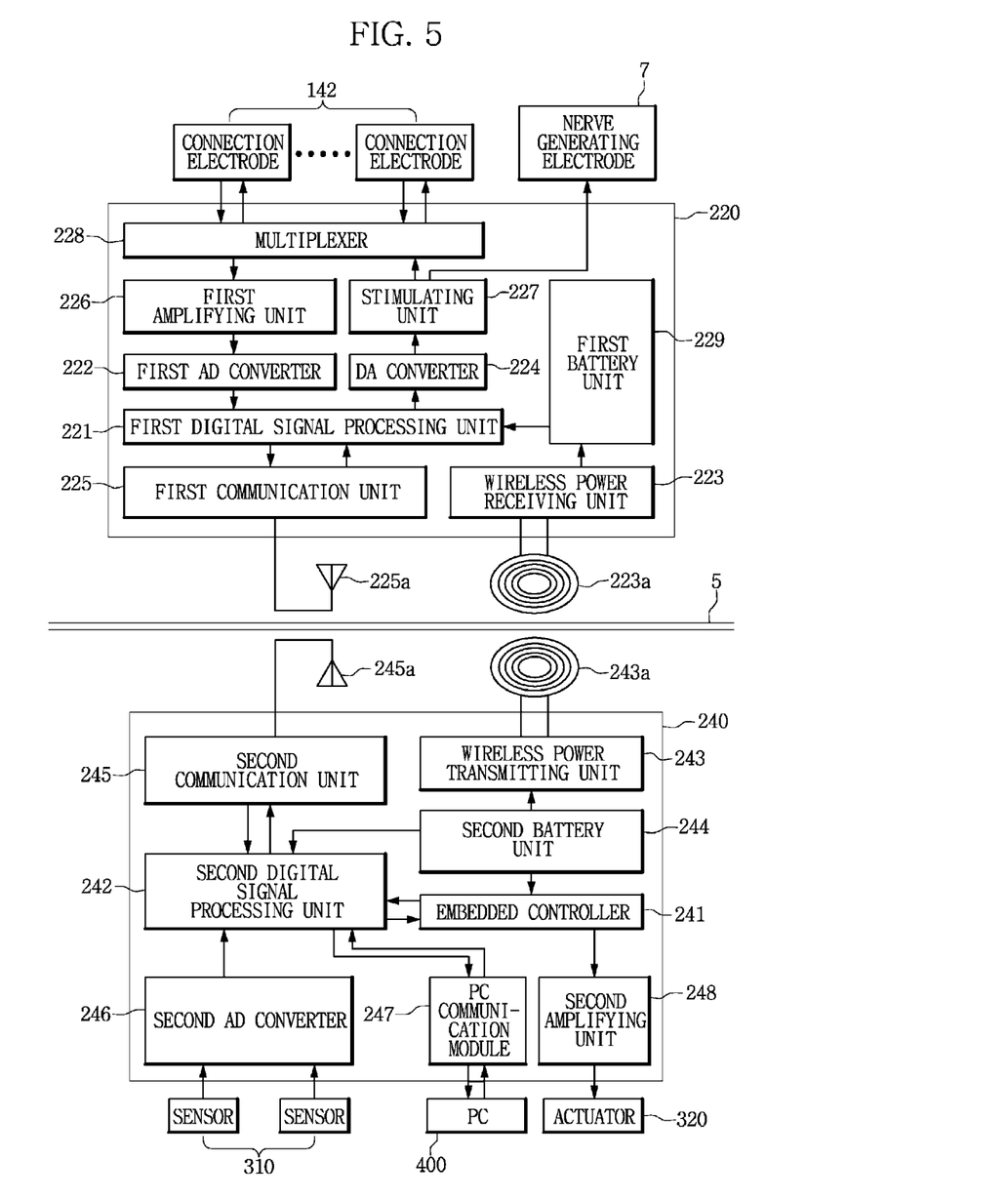
FIG. 5 is a detailed diagram showing a peripheral nerve interface unit applied to the peripheral nerve interface system according to an embodiment of the present disclosure.

FIG. 5 is a detailed diagram showing a peripheral nerve interface unit applied to the peripheral nerve interface system according to an embodiment of the present disclosure.

Referring to FIG. 5, the peripheral nerve interface unit 200 includes an internal module 220 and an external module 240.

The internal module 220 includes a first digital signal processing unit 221, a first AD converter 222, a DA converter 224, a first amplifying unit 226, a stimulating unit 227, a multiplexer 228, a first communication unit 225, a wireless power receiving unit 223 and a first battery unit 229.

The roles of the first digital signal processing unit 221, the first amplifying unit 226, the stimulating unit 227, the first communication unit 225 and the nerve regenerating electrode 7 have been described in relation to FIG. 1 and thus are not described in detail here.

The multiplexer 228 plays a role of selectively matching the efferent motor nerve signals received from a plurality of 'connection electrodes', namely the second connection unit 142, with a limited number of the first amplifying units 226 and the stimulating units 227.

The multiplexer 228 performs this matching operation according to an instruction of the first digital signal processing unit 221, and the first digital signal processing unit 221 performs such operations by using the multilayer perceptron algorithm.

The first AD converter 222 converts the efferent nerve signal amplified by the first amplifying unit 226 from an analog signal to a digital signal so that the first digital signal processing unit 221 may analyze the efferent nerve signal.

The DA converter 224 plays a role of converting the digital signal transferred from the first digital signal processing unit 221 into an analog signal.

As described above in relation to FIG. 1, the first communication unit 225 plays a role of transmitting and receiving the efferent motor nerve signal and the afferent sensory signal to/from the second communication unit 245 of the external module 240 in a wireless communication manner. As shown in FIG. 5, the first communication unit 225 may include an RF antenna 225a.

The wireless power receiving unit 223 receives power from the external module 240 in a wireless manner and supplies the power to the first battery unit 229. The first battery unit 229 is charged with the supplied power and supplies power to the first digital signal processing unit 221 or the like.

As shown in FIG. 5, the wireless power receiving unit 223 may include a power coil 223a for receiving power. The power coil 223a of the wireless power receiving unit 223 is supplied with power from the power coil 243a of the wireless power transmitting unit 243 of the external module 240 in a wireless communication manner. The wireless power transmission method using electromagnetic induction is well known in the art and thus not described in detail here.

The external module 240 includes an embedded controller 241, a second digital signal processing unit 242, a wireless power transmitting unit 243, a second battery unit 244, a second communication unit 245, a second AD converter 246, a PC communication module 247 and a second amplifying unit 248.

The second battery unit 244 supplies power to the second digital signal processing unit 242 or the like, and the wireless power transmitting unit 243 receives power from the second battery unit 244 and supplies the power to the wireless power receiving unit 223 of the internal module 220 in a wireless manner. The wireless power transmitting unit 243 includes a power coil 243a, similar to the internal module 220.

The second communication unit 245 plays a role of transmitting and receiving signals to/from the first communication unit 225 of the internal module 220 and is configured to include an RF antenna 245a.

The second AD converter 246 plays a role of receiving the sensory signal detected by the sensor 310 of the prosthesis 300 and converting the sensory signal into a digital signal.

The second digital signal processing unit 242 plays a role of receiving the digital signal from the second communication unit 245 and the second AD converter 246 and then analyzing and processing the digital signal. In detail, the second digital signal processing unit 242 analyzes the efferent motor nerve signal of the peripheral nerve 10 received by the second communication unit 245, and transmits the analysis result to the embedded controller 241 in order to control the prosthesis 300. In addition, the second digital signal processing unit 242 analyzes the sensory signal converted into the digital signal by the second AD converter 246 and transmits the sensory signal to the internal module 220 through the second communication unit 245.

The embedded controller 241 receives the efferent motor nerve signal from the second digital signal processing unit 242 as described above, and then generates an actuator control signal corresponding thereto and transmits the actuator control signal to the second amplifying unit 248.

The second amplifying unit 248 amplifies the received actuator control signal and transfers the amplified actuator control signal to an actuator 320 of the prosthesis 300. The actuator 320 is a module for controlling a joint of the prosthesis 300 and is installed in the prosthesis 300.

The PC communication module 247 is installed to operate the external module 240 in linkage with an external PC 400. In other words, the external module 240 may be connected to the external PC 400 through the PC communication module 247 to provide a user with the processing situation of the second digital signal processing unit 242 through a screen of the PC 400.

Figure 6:
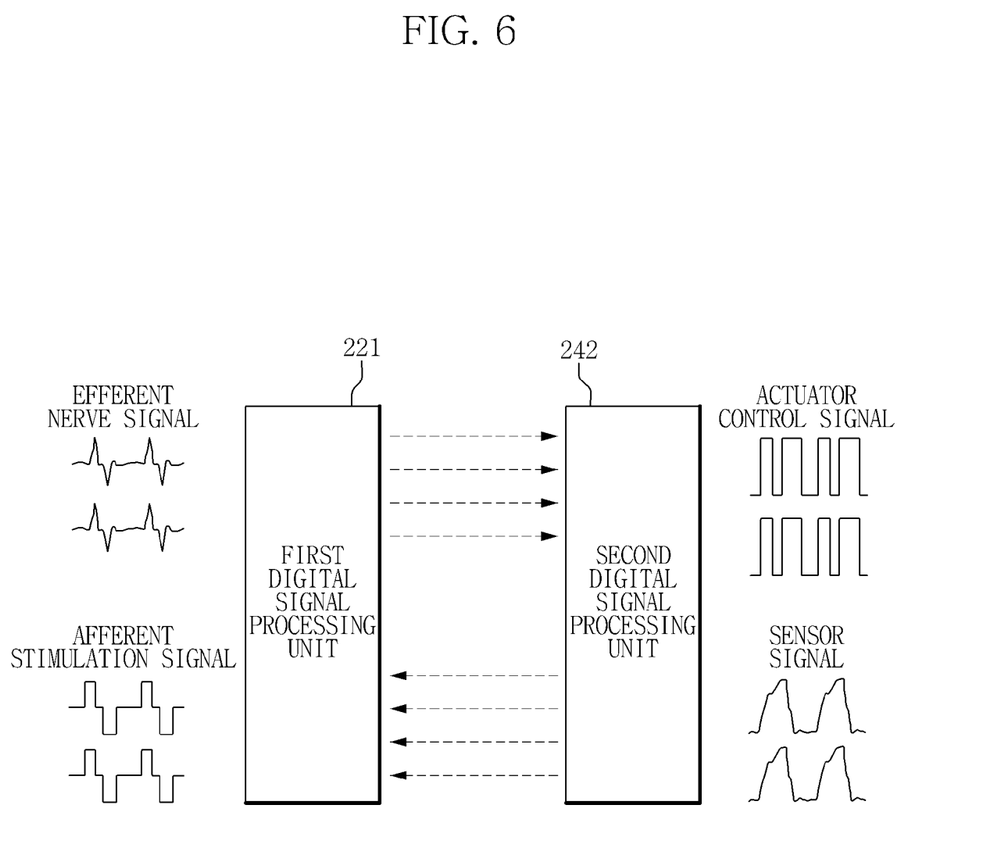
FIG. 6 is a conceptual diagram for illustrating a signal transmission operation of the peripheral nerve interface system according to an embodiment of the present disclosure.

FIG. 6 is a conceptual diagram for illustrating a signal transmission operation of the peripheral nerve interface system according to an embodiment of the present disclosure.

The first digital signal processing unit 221 of the internal module 220 and the second digital signal processing unit 242 of the external module 240 transmit or receive signals in a wireless manner. The first digital signal processing unit 221 receives the efferent motor nerve signal generated by the peripheral nerve 10 of the cut body portion of a patient and transmits the efferent motor nerve signal to the second digital signal processing unit 242. The second digital signal processing unit 242 generates an actuator control signal corresponding to the efferent motor nerve signal to control operations of the prosthesis 300.

On the contrary, the second digital signal processing unit 242 receives the sensory signal detected by the sensor 310 of the prosthesis 300 and converts the sensory signal into a digital signal, and transmits the converted signal to the first digital signal processing unit 221.

Then, the first digital signal processing unit 221 generates an afferent electric stimulation signal corresponding to the sensory signal and transfers the afferent electric stimulation signal to a nerve cell regenerated at the terminal of the peripheral nerve 10.

The electric stimulation pattern is formed by applying afferent electric stimulation pulses to a peripheral nerve regenerated at a nerve electrode located in the porous polymer nerve conduit 100. The regenerated peripheral nerve is classified into an efferent axon and an afferent axon.

Therefore, the peripheral nerve interface unit 200 sets paths according to the kinds of efferent axons to propagate efferent signals and afferent signals so that the efferent nerve electrode may be connected to the amplifying unit 226 and the afferent nerve electrode may be connected to the stimulating unit 227. The path setting method may adopt a multilayer perceptron algorithm widely known in the art.

The input/output of the peripheral nerve interface algorithm are set according to the path setting, and accordingly the prosthetic hand, namely the prosthesis 300, is bound as a single closed loop, which may overcome the limit of an existing open loop.

Figure 7:
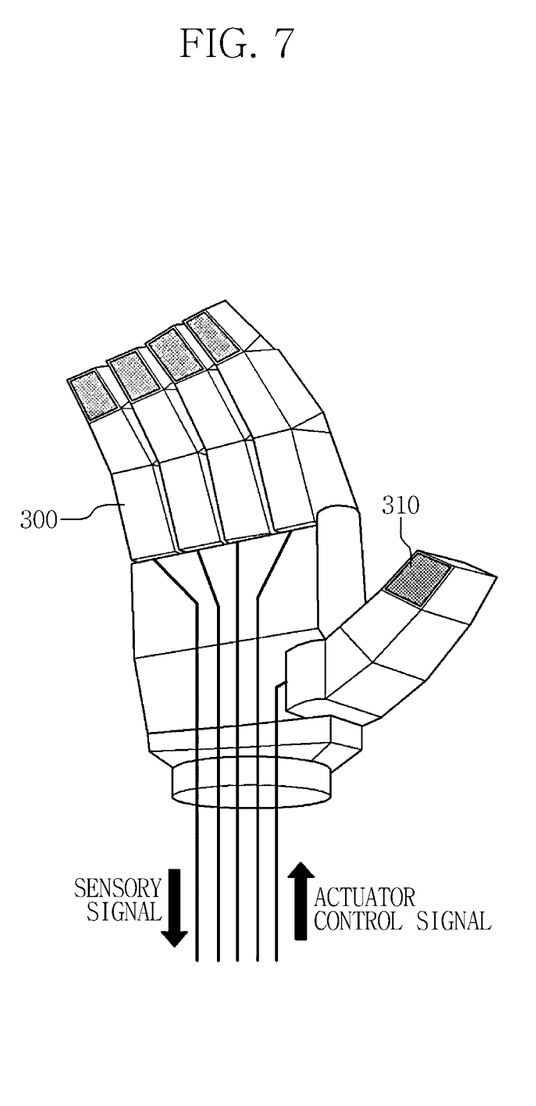
FIG. 7 is a diagram showing a prosthesis applied to the peripheral nerve interface system according to an embodiment of the present disclosure.

FIG. 7 is a diagram showing a prosthesis applied to the peripheral nerve interface system according to an embodiment of the present disclosure.

FIG. 7 depicts a prosthetic hand model as an example of the prosthesis 300. The prosthesis 300 may have multiple joints and multi-degree of freedom for natural movement and may be designed similar to a hand or foot of a human.

The sensor 310 for measuring a sensory signal is installed at the prosthesis 300 of FIG. 7, namely at the finger of the prosthetic hand, and the measured sensory signal is analyzed at the digital signal analyzing unit of the peripheral nerve interface unit 200 and transferred as an afferent nerve signal.

In addition, according to the efferent motor nerve signal transmitted from the internal module 220, the embedded controller 241 of the external module 240 generates and transmits the actuator control signal for controlling the prosthesis 300.

The peripheral nerve interface system and method according to the present disclosure controls a prosthetic hand by using the feedback of a nerve signal of the peripheral nerve remaining at the cut portion and a sensory signal measured by the sensor of the prosthetic hand, thereby allowing the prosthetic hand to be controlled similar to actual hand movements.

While the exemplary embodiments have been shown and described, it will be understood by those skilled in the art that various changes in form and details may be made thereto without departing from the spirit and scope of the present disclosure as defined by the appended claims.

What is claimed is:

1. A peripheral nerve interface system, comprising:
a nerve conduit configured to be connected to a terminal of a damaged peripheral nerve at a cut body portion;
a prosthesis for substituting for the cut body portion; and
a peripheral nerve interface unit electrically connected to the nerve conduit and the prosthesis to restore a function of the damaged peripheral nerve and control operations of the prosthesis by transmitting and receiving signals of the damaged peripheral nerve,
wherein the nerve conduit comprises:
a support connected to the terminal of the damaged peripheral nerve;
a channel formed in a body of the support and having a cavity shape;
an electrode layer formed along an inner wall of the channel; and
an external electrode electrically connected to the electrode layer,
wherein the channel is configured for permitting growth of a nerve cell along the channel at the terminal of the damaged peripheral nerve, and the electrode layer is configured to electrically connect to the nerve cell having grown along the channel,
wherein the support comprises a plurality of channels, and the peripheral nerve interface unit comprises:
an internal module configured for being implanted into a damaged body portion and electrically connected to the nerve conduit; and
an external module configured for being positioned out of the damaged body portion and electrically connected to the prosthesis,
wherein the internal module and the external module are configured for transmitting and receiving nerve signals to/from each other in a wireless communication manner, and the internal module comprises:
a first amplifying unit for amplifying the signal of the damaged peripheral nerve received through the nerve conduit;
a first AD converter for converting the signal amplified by the first amplifying unit into a digital signal;
a first digital signal processing unit for receiving and analyzing the digital signal converted by the first AD converter and transmitting the digital signal to the external module in a wireless communication manner, or receiving and analyzing the digital signal received from the external module and transmitting the digital signal to the grown nerve cell through the channel;
a DA converter for converting the digital signal received by the first digital signal processing unit into an analog signal;
a stimulating unit for transferring an electric stimulation signal to the grown nerve cell along the plurality of channels by using the analog signal converted by the DA converter;
a multiplexer for electrically matching a plurality of nerve cells having grown along the plurality of channels according to an instruction of the first digital signal processing unit with the first amplifying unit and the stimulating unit; and
a first communication unit for transmitting and receiving signals to/from the external module in a wireless communication manner, and
wherein the first digital signal processing unit is configured for adopting a multilayer perceptron algorithm.

2. The peripheral nerve interface system of claim 1, wherein the internal module further comprises:
a first battery unit for supplying power to the internal module; and
a wireless power receiving unit for receiving power from the external module in a wireless manner and transferring the power to the first battery unit.

3. The peripheral nerve interface system of claim 1, further comprising a nerve regenerating electrode connected to the damaged peripheral nerve,
wherein the stimulating unit transfers a nerve generating stimulation signal to the nerve regenerating electrode.

4. The peripheral nerve interface system of claim 1, wherein the external module comprises:
a second communication unit for transmitting and receiving a signal to/from the internal module in a wireless communication manner;
a second AD converter for converting an analog signal received by a sensor installed at the prosthesis into a digital signal;
a second digital signal processing unit for analyzing and processing the signal of the peripheral nerve received by the second communication unit and transmitting the signal to the internal module through the second communication unit based on the signal received by the second AD converter;
an embedded controller for controlling operations of the prosthesis based on the signal processed by the second digital signal processing unit; and
a second amplifying unit for amplifying a control signal of the embedded controller and transferring the amplified control signal to the prosthesis.

5. The peripheral nerve interface system according to claim 4, wherein the external module further includes:
a second battery unit for supplying power to the external module; and a wireless power transmitting unit for receiving power from the second battery unit and transmitting the power to the internal module in a wireless manner.

6. The peripheral nerve interface system according to claim 1, wherein the prosthesis includes at least one sensor for detecting a sensory signal.

7. A peripheral nerve interface method, comprising:
regenerating a nerve cell at a terminal of a damaged peripheral nerve of a cut body portion by using a nerve conduit;
detecting an efferent motor nerve signal by using an internal module implanted in the cut body portion and electrically connected to the nerve conduit;
transmitting the efferent motor nerve signal to an external module located out of the cut body portion;
controlling an operation of a prosthesis which substitutes for the cut body portion by using the external module
detecting, by a sensor installed at the prosthesis, an afferent sensory signal;
analyzing, by the external module the detected afferent sensor signal;
receiving, by the internal module, the afferent sensory signal from the external module; and
generating, by the internal module, an electric stimulation signal corresponding to the afferent sensory signal and transferring the electric stimulation signal through the nerve conduit to the nerve cell at the terminal of the peripheral nerve.

8. The peripheral nerve interface method of claim 7, further comprising:
transferring, by the internal module, a nerve generating stimulation signal to a nerve regenerating electrode connected to the damaged peripheral nerve.

9. The peripheral nerve interface method of claim 7, wherein the nerve conduit includes a porous polymer electrode,
wherein the method comprises:
selectively detecting the efferent motor nerve signal or the afferent sensory nerve signal by using the porous polymer electrode; and
selectively transferring an electric stimulation signal to the nerve cell at the terminal of the damaged peripheral nerve.

10. The peripheral nerve interface method according to claim 9, wherein said selectively detecting of the efferent motor nerve signal or the afferent sensory nerve signal and said selectively transferring of an electric stimulation signal to the nerve cell at the terminal of the damaged peripheral nerve are performed by using a multilayer perceptron algorithm.

* * * * *